United States Patent [19]
Hoerner et al.

[11] Patent Number: 5,883,155
[45] Date of Patent: Mar. 16, 1999

[54] ELASTOMER FILMS CONTAINING AT LEAST ONE ACTIVE CHEMICAL SUBSTANCE, PROCESS FOR THEIR PREPARATION AND THEIR APPLICATIONS

[75] Inventors: Pierre Hoerner, Horbourg-Winr; Gérard Riess, Mulhouse; René Guy Busnel, Bièvres; André Cheymol, Dange Saint Romain, all of France

[73] Assignee: Hutchinson, Paris, France

[21] Appl. No.: 740,898

[22] Filed: Nov. 4, 1996

[30] Foreign Application Priority Data

Nov. 2, 1995 [FR] France ................................ 95 12926

[51] Int. Cl.⁶ .............................. C08L 1/28; C08L 5/12; C08L 89/00; C08K 5/15
[52] U.S. Cl. ............................. 523/122; 524/22; 524/28; 524/43; 524/44; 524/45; 524/46; 524/55; 524/110; 524/377; 524/503; 524/505; 524/556; 524/555; 524/557; 524/916
[58] Field of Search ...................... 523/122; 524/22, 524/28, 43, 44, 45, 46, 55, 110, 377, 555, 556, 557, 503, 505, 916

[56] References Cited

U.S. PATENT DOCUMENTS 4,362,841 12/1982 Minatono et al. ................... 524/916
4,952,618 8/1990 Olsen ................................ 524/28
5,000,955 3/1991 Gould et al. ....................... 524/916
5,011,875 4/1991 Yamamoto et al. ................. 524/916
5,277,915 1/1994 Provonchee et al. ............... 523/122

FOREIGN PATENT DOCUMENTS

| A -0 306 389 | 3/1989 | European Pat. Off. . |
| 0 557 625 A1 | 9/1993 | European Pat. Off. . |
| 2 263 114 A | 7/1993 | United Kingdom . |
| WO 95/17453 | 6/1995 | WIPO . |

*Primary Examiner*—Peter A. Szekely
*Attorney, Agent, or Firm*—Oblon, Spivak, McClelland, Maier & Neustadt, P.C.

[57] ABSTRACT

Elastomer films in which active chemical substances, such as corrosion inhibitors, lubricants or biocides for medical use are uniformly dispersed in the form of gel inclusions, processes for preparation and applications of these films.

The elastomer film contains at least one active chemical substance in the form of a phase which is dispersed in the elastomer, wherein the disperse phase is in the form of a gel, reversible or irreversible, as a function of temperature, and filled with an active chemical substance.

16 Claims, 4 Drawing Sheets

VIRUCIDE (X)

SOLVENT (DS)

STRUCTURING POLYMER (C)

FIG. 5

ELASTOMER FILMS CONTAINING AT LEAST ONE ACTIVE CHEMICAL SUBSTANCE, PROCESS FOR THEIR PREPARATION AND THEIR APPLICATIONS

BACKGROUND OF THE INVENTION

Field of the Invention

The present invention relates to elastomer films in which active chemical substances such as corrosion inhibitors, lubricants or biocides for medical use are uniformly dispersed in the form of gel inclusions as well as processes of preparation and various applications for these films.

The present invention also relates to stable dispersions containing a continuous phase formed by a solution of elastomer in an organic solvent and a disperse phase including at least one active chemical substance included in a gel, which dispersions are capable of being converted into elastomer film, and to the process for their preparation.

DISCUSSION OF THE BACKGROUND

The various elastomeric materials usually employed in the medical or paramedical field, particularly hygiene, can be modified so as to be used in combination with chemical substances which have a protective effect when these materials, i.e. gloves, fingerstalls, sheaths or diaphragms and various bandages and dressings, for example, are employed, as illustrated in European Patent 306 389 or the International Application WO 95/17453, which describe elastomer films incorporating at least one active chemical substance either in the form of liquid inclusions stabilized by a block or graft copolymer (International Application WO 95/17453) or contained in microcapsules the walls of which break under the action of rubbing or shearing forces. (European Patent 306 389).

However, these elastomer films exhibit several disadvantages.

First, deterioration, over time, in the performance of the materials obtained can be observed in the case of microcapsules, on the one hand, because of chemical reactions that can occur between the active substances within the disperse phase and, on the other hand, because of diffusion of these same substances outside of the microcapsule.

Second, the microcapsules contained in the elastomer films according to European Patent 306 389 can present difficulties in breaking, in order to release their active substances, when the films are perforated.

Third, the elastomer films containing liquid inclusions according to International Application WO 95/17453 make use of graft or block copolymer macromolecular stabilizers which are quite costly.

Thus, a need exists for an elastomer material which overcomes the above disadvantages.

SUMMARY OF THE INVENTION

Accordingly, it is an object of the present invention to provide an elastomer material which responds better to the requirements of practice than do all the elastomers of the prior art, particularly in their storage behavior and reduced expense.

DETAILED DESCRIPTION OF THE PREFERRED EMBODIMENTS

The present invention is predicated upon the surprising discovery that, when active chemical molecules are incorporated in a gel, the dispersion of the gel in an elastomer (solution and film) is stable, does not require the use of stabilizing agents, i.e. compatibilizing agents, such as the block or graft copolymers described in International Application WO 95/17453, and results in a flexible elastomeric material being obtained.

Thus, the present invention provides an elastomer film containing at least one active chemical substance in the form of a phase which is dispersed in the elastomer, wherein the disperse phase of the film is in the form of a gel, reversible or irreversible as a function of the temperature, and filled with active chemical substance x.

According to the literature, i.e., *Encyclopedia of Polymer Science and Engineering*, 2nd edition: Wiley Interscience; Volume 7 and Suppl. Vol., a gel can be defined as being a polymeric network corresponding to an intermediate transition state between a liquid and a solid.

Gels which are irreversible as a function of temperature, are formed chemically, i.e., by covalent crosslinking, whereas gels which are reversible, as a function of temperature, are formed either physically, that is to say by interaction of the hydrogen, van der Weals or dipole-dipole bond type, or by formation of a complex or of crystalline domains.

With reversible gels, a transition occurs at a critical temperature (Ttrans) at which the physical interactions disappear. The gel-liquid transformation corresponds to this transition.

According to the above-mentioned literature reference, the formation of a gel is easily detected as a change in the viscosity or elasticity of the system.

In accordance with the present invention, the gel consists essentially of a structuring polymer c, a solvent $d_s$, and at least one active chemical substance x.

According to one advantageous embodiment of the present elastomer film, when the gel is reversible, a gel-liquid transition temperature (Ttrans) of between 0° C. and 120° C., preferably between 20° C. and 70° C., is observed.

According to an advantageous arrangement of this embodiment, the reversible gel consists essentially of a structuring polymer c, a solvent $d_s$ and at least the active chemical substance x; however, it may additionally contain a reversible crosslinking agent $d_{rc}$.

The crosslinking may take place either by intermolecular interaction between the chains (hydrogen or dipole-dipole bonds, partial crystallization) of the structuring polymer c or by addition of a crosslinking agent $d_{rc}$ causing the formation of physical bonds (complexes, hydrogen bonds or force of dipole-dipole type) between the chains of structuring polymer c.

According to an advantageous method of this arrangement, the structuring polymer c is of hydrophilic type and immiscible with the elastomer phase.

In accordance with this aspect of the present invention, the structuring polymer c may be either a crystallizable or partially crystallizable polymer, such as, for example, polyethers, preferably from polyoxyethylenes, of molecular mass of between 1,500 and $10^6$ daltons and polyoxyethylene-based polymers exhibiting, in the molten state, a miscibility with the solvent $d_s$, or of polymers which are not organized in the solid state, such as, for example, polymers of natural origin such as gelatin, gums, pectins, and alginates, as well as some cellulose derivatives like methyl cellulose, hydroxyethyl cellulose, hydroxypropyl cellulose and carboxymethyl cellulose, and it can even be one or more synthetic compounds like polyethyleneimine, polyacrylic acid, polyacrylates and polymethacrylates such as poly(hydroxyethyl methacrylate), polyvinyl alcohol and its derivatives and polyvinyl ethers, such as poly(vinyl methyl ether).

According to another advantageous method of this arrangement, the solvent $d_s$ is preferably one or more of the polyols, preferably from ethylene glycol, glycerine and polyethylene glycols which are liquid at ambient temperature and of a molecular mass of between 62 (ethylene glycol) and 750 daltons (PEG750) and water, which are employed alone or as a mixture.

According to still another advantageous method of this arrangement, the crosslinker $d_{rc}$ is preferably one of certain derivatives of boron, such as boric acid or borax, of aluminum, like alumina hydrate or certain aluminum hydroxides, and of certain divalent metals like zinc or calcium; it is employed as a crosslinker of the structuring polymer c and acts by forming physical bonds between the chains of the structuring polymer c.

Further, when the gel is of an irreversible type and consequently does not exhibit any transition temperature Ttrans, it consists essentially of a structuring polymer c, a solvent $d_s$, a crosslinker $d_{ic}$ (irreversible crosslinker) and at least one active chemical substance x.

The crosslinking takes place by covalent chemical bonding, that is to say irreversibly, between the chains of the structuring polymer c.

It is, moreover, advantageous if the structuring polymer c is of hydrophilic type and immiscible with the elastomer phase. Thus, it is preferable if, for this aspect of the present invention, the structuring polymer c is one or more of polymers of natural origin like gelatin, gums, pectins and alginates or certain cellulose derivatives like methyl cellulose, hydroxyethyl cellulose, hydroxypropoyl cellulose and carboxymethyl cellulose and synthetic compounds like polyethyleneimine, polyacrylic acid, polyacrylates and polymethacrylates such as poly(hydroxyethyl methacrylate), polyvinyl alcohol and its derivatives and poly(vinyl ethers) like poly(vinyl methyl ether).

According to yet another advantageous arrangement of this embodiment, the compound $d_s$ may be one of the polyols, preferably from ethylene glycol, glycerine and more generally the polyethylene glycols which are liquid at ambient temperature and of molecular mass of between 62 (ethylene glycol) and 750 daltons (PEG750) and water, which are employed alone or as a mixture.

Further, it is preferable if the crosslinker $d_{ic}$ is an aldehyde or dialdehyde of low or of high molecular weight like, for example, glyoxal, but may be any other compound capable of reacting chemically with the structurant c, such as, for example, urea-formaldehyde or melamine-formaldehyde derivatives.

According to still another advantageous embodiment of the elastomer film, the active chemical substance x is a compound capable of causing a virtually instantaneous denaturing of the proteins by simple contact, either by chemical reaction or by a physicochemical effect such as a change in the surface tension. This class of compounds includes, among others, the biocides.

According to an advantageous arrangement of this embodiment, the biocide may be a quaternary ammonium, preferably dimethyldidecylammonium, biguanides, phthaldahyde, phenolic derivatives, formalin, nonionic surfactants containing at least one polyoxyethylene block, hexamidine, iodine compounds, for example the iodine complex of polyvinylpyrrolidone, nonionic surfactants with virucidal activity and sodium and potassium dichromates and hypochlorites, employed alone or as a mixture.

According to still another advantageous embodiment of the elastomer film, the gel includes:

A. when the gel is crosslinked reversibly:
  i) between about 25 and 97% (mass content) of solvent $d_s$, relative to the gel, preferably between about 25 and 98% (mass content).
  ii) between about 1 and 74% (mass content) of the structuring polymer between c, relative to the gel,
  iii) between about 1 and 74% (mass content) of the said active chemical substance x, relative to the gel, and
  iv) between about 0 and 1% of crosslinker $d_{rc}$ (crosslinker mass content/total constituents), preferably between about 0 and 0.1%.

B. when the gel is crosslinked irreversibly:
  i) between about 25 and 98% (mass content) of solvent $d_s$ relative to the gel, preferably between about 25 to 97% (mass content)
  ii) between about 1 and 74% (mass content) os structuring polymer c relative to the gel,
  iii) between about 1 and 74% (mass content) of active chemical substance x relative to the gel, and
  iv) between about 0.0001 and 1% of crosslinking agent $_{ic}$ (crosslinker mass ratio/total constituents), preferably between about 0.0001 and 0.1%.

The elastomer may be polybutadiene, polyisoprene and the SBR (styrene butadiene rubber), NBR (nitrile butadiene rubber), SBS (styrene butadiene styrene), SIS (styrene isoprene styrene) or SEBS (styrene ethylene butylene styrene) copolymers, for example. This list is only exemplary and not intended to be limitative.

According to another advantageous embodiment of the elastomer film, the mass proportions of the elastomer and of the gel are the following:
  elastomer: between about 20 and 95% (mass content), expressed in relation to the final film, and
  gel: between about 5 and 80% (mass content), expressed in relation to the final film.

The present invention also provides a process for the preparation of the elastomer film, which entails:
  1) preparation of a dispersion of a gel, which includes:
    the preparation of a phase A by dissolving the elastomer in an organic solvent a;
    the preparation of a phase B (gel) and the dispersion of the phase B in the phase A, according to one of the following methods:
  A. when the gel is crosslinked reversibly:
    the phase B can be prepared according to two different ways, according to whether crosslinker $d_{rc}$ is or is not employed:
    (i) in the case where the gel is formed spontaneously by bonds of physical type, the phase B is prepared by mixing at least one active chemical substance x in a solvent $d_s$, followed by mixing of the solution obtained with a polymer c, at a temperature higher than the transition temperature Ttrans, corresponding to the gel-liquid transition, which temperature Ttrans is between about 0° C. and 120° C., preferably between about 20° C. and 120° C., followed by the dispersion of the phase B in the phase A, at a temperature higher than Ttrans; the size of the gel inclusions can be adjusted as a function of the speed of stirring and of the rate of cooling of the dispersion;

(ii) in the case where the addition of a crosslinker $d_{rc}$ is necessary for the formation of the reversible gel, the phase B is prepared by mixing at least one active chemical substance x in a solvent $d_s$, followed by mixing of the solution obtained with a structuring polymer c. This phase B is dispersed in the phase A before addition of the crosslinker $d_{rc}$;

B. when the gel is crosslinked irreversibly:
  the phase B is obtained by mixing at least one active chemical substance x in a solvent $d_s$, followed by mixing of the solution obtained with a structuring polymer c, and then this phase B is dispersed in the phase A before addition of the crosslinking agent $d_{ic}$, and 2) evaporation of the organic solvent a, to obtain an elastomer film enclosing gel inclusions in a stable dispersion form.

In the case of a gel which is crosslinked reversibly, the evaporation of the solvent is performed at a temperature lower than Ttrans and the elastomer film encloses gel inclusions including the polymer c, the solvent $d_s$ and optionally the crosslinker $d_{rc}$, and is filled with active chemical substance x.

In the case of a gel which is crosslinked irreversibly, the evaporation of the solvent is performed at a temperature chosen as a function of the desired evaporation time and included between 0 and 120° C., and the elastomer film encloses gel inclusions including the polymer c, the solvent $d_s$, the crosslinker $d_{ic}$ and is filled with active chemical substance x.

According to an advantageous embodiment of the present process, the apolar or weakly polar solvent a may be aromatic, aliphatic and alicyclic hydrocarbons, for example paraffinic hydrocarbons, cyclohexane, benzene, toluene, xylene, tetralin, decalin, petroleum cuts (made up predominantly of cylcic aliphatic hydrocarbons and characterized by their boiling temperature), or a mixture of these.

In accordance with the process according to the invention the structuring polymer c, the solvent $d_s$, the crosslinking agents $d_{rc}$ or $d_{ic}$ and the active chemical substance x are as defined above.

The present invention also provides a dispersion capable of being employed for the preparation of an elastomer film in accordance with the invention, which includes:

a phase A containing an elastomer dissolved in an organic solvent a (hydrophobic or apolar phase) as defined above, in which is dispersed, in the form of a reversible or irreversible gel, a phase B including an active chemical substance x included in a structuring polymer c, a solvent $d_s$, and optionally a crosslinking agent $d_{rc}$ or $d_{ic}$, as defined above.

Such dispersions exhibit a stability to sedimentation of at least 12 hours at ambient temperature, whereas the stability of the films in storage (that is to say conservation of the virucidal effectiveness and of the structure) is much longer than a year.

The present invention also provides a process for the preparation of the said stable dispersions, which includes:

the preparation of a phase A by dissolving the elastomer in an organic solvent a;

the preparation of a phase B (gel), which may be carried out according to two different methods, according to the type of gel:

in the case where the gel is crosslinked reversibly, that is to say exhibits a gel-liquid transition temperature Ttrans, the phase B is obtained:

if the gel is formed spontaneously by bonding of physical type, the phase B is prepared by mixing at least one active chemical substance x in a solvent $d_s$, followed by mixing of the solution obtained with a structuring polymer c, at a temperature higher than the transition temperature Ttrans, corresponding to the gel-liquid transition, which temperature Ttrans is between about 20° C. and 120° C. This phase B is next dispersed in the phase A at a temperature higher than Ttrans. The size of the gel inclusions is controlled by the stirring speed and by the cooling rate;

in the case where the addition of a crosslinking agent $d_{rc}$ is necessary for the formation of the reversible gel, the phase B is prepared by mixing at least one active chemical substance x in a solvent $d_s$ followed by mixing of the solution obtained with a structuring polymer c. This phase B is dispersed in the phase A before addition of the crosslinking agent $d_{rc}$, in the case where the gel is crosslinked irreversibly, the phase B is obtained by mixing at least one active chemical substance x in a solvent $d_s$, followed by mixing of the solution obtained with a structuring polymer c; this phase B is dispersed in the phase A before addition of the crosslinking agent $d_{ic}$.

The present invention also provides various applications of the present elastomer film as a coating for supports especially made of elastomer or of plastic or for overmoulding a friction joint.

The present invention may be further understood by reference to FIGS. 1–5 which we further described as follows.

Figure 1:
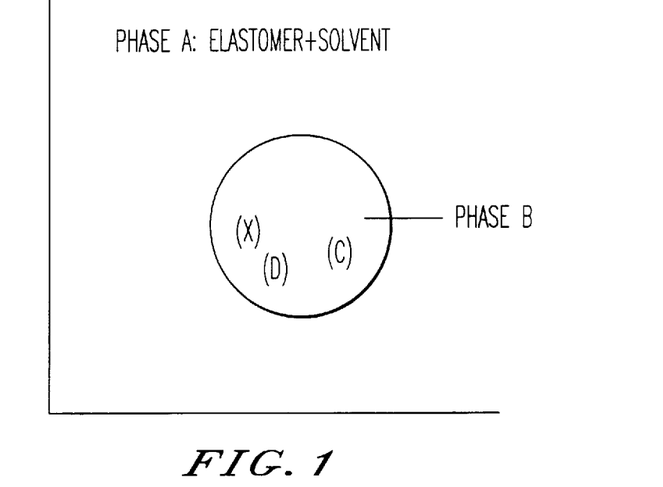
FIG. 1 illustrates the structure of the present gel dispersion in a solvent medium.

FIG. 1 illustrates the structure of the gel dispersion in a solvent medium.

Figure 2:
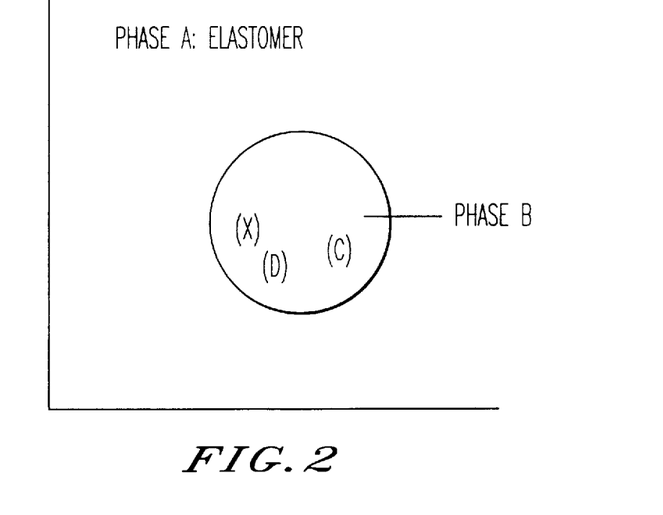
FIG. 2 illustrates the structure of the present gel dispersion in the dry film.

FIG. 2 illustrates the structure of the gel dispersion in the dry film.

Figure 3:
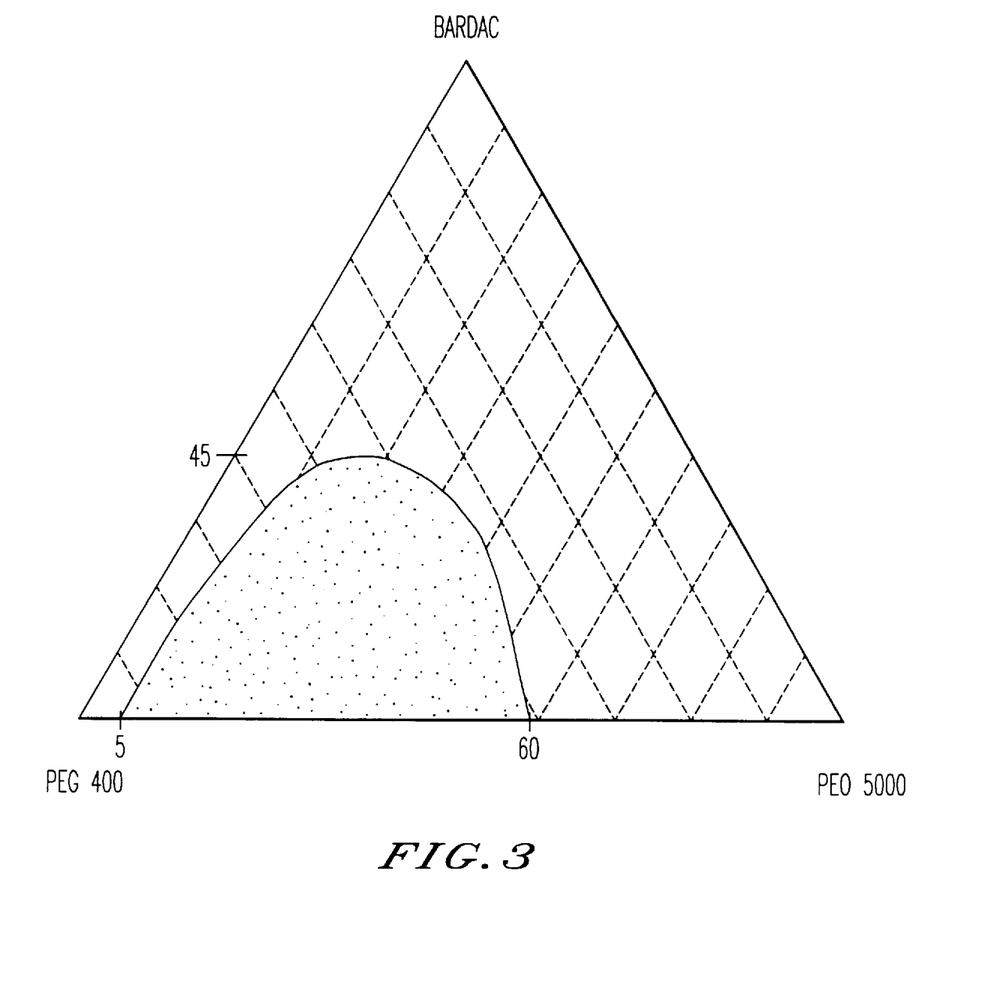
FIG. 3 and 4 illustrate the combination of polymer c, active substance x and $d_s$ mixture and the boundaries of the domain of existence.
Figure 4:
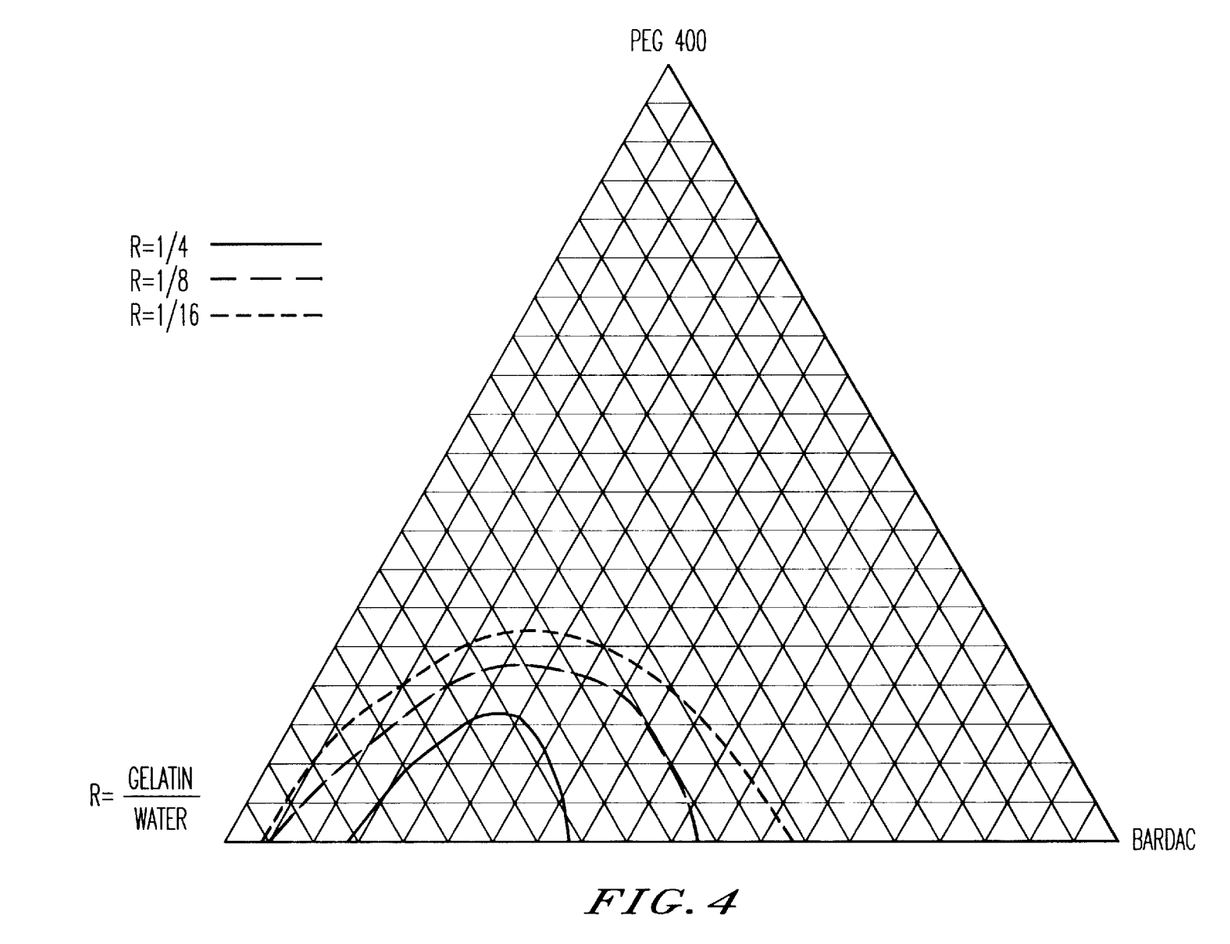

FIGS. 3 and 4 illustrate the combinations of the polymer c, active substance x and $d_s$ mixture and the boundaries of the domain of gel existence (for example PEO 5000, Bardac® and PEG400 (FIG. 4) resulting in a gel at ambient temperature (ternary diagram).

Figure 5:
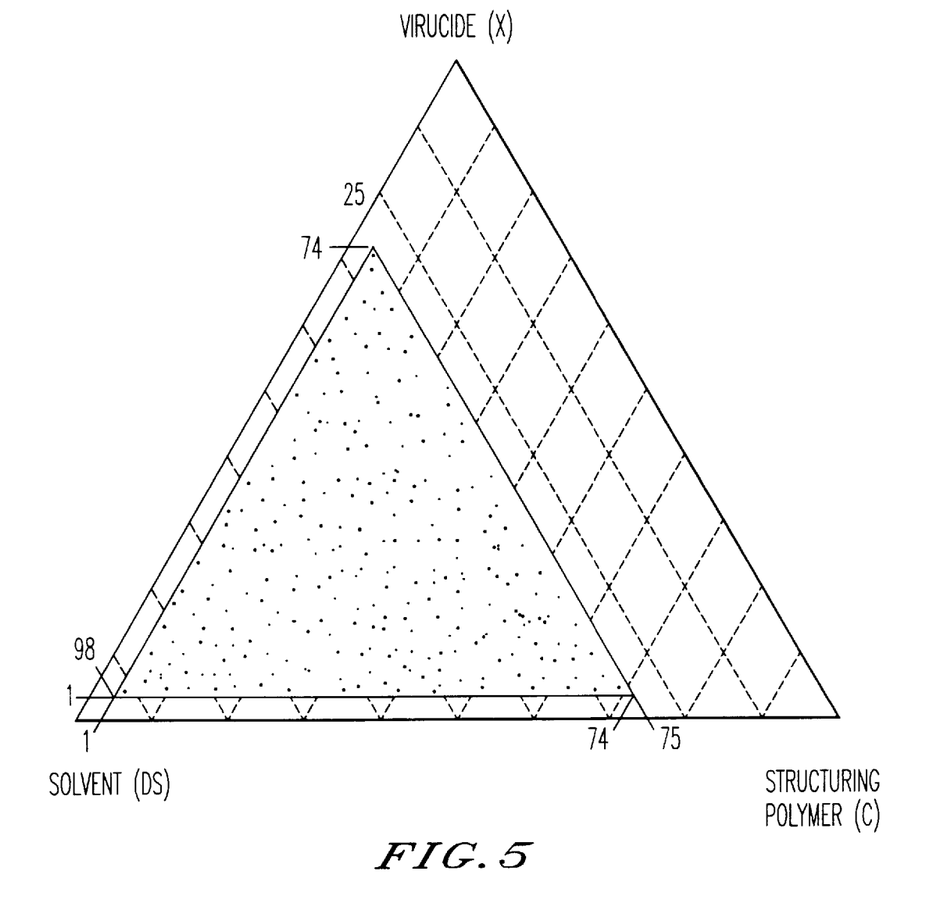
FIG. 5 illustrates the boundary of gel existence containing a structuring polymer c, an active chemical substance x and a solvent $d_s$.

FIG. 5 illustrates the boundary of the domain of gel existence containing a structuring polymer c, an active chemical substance x and a solvent $d_s$. This figure shows the case of a reversible gel without crosslinking agent $d_{rc}$, in this figure the shaded domain corresponds to the claimed domain of composition.

The present invention will now be further illustrated by reference to certain examples which are provided solely for purposes of illustration and are not intended to be limitative.

EXAMPLE 1

An elastomer film according to the present invention based on polyisoprene containing inclusions of a reversible gel including PEO 5000 as structuring polymer c and not comprising any crosslinking agent $d_{rc}$.

i) Preparation of a stable gel dispersion

Preparation of the continuous phase (Phase A)

Synthetic polyisoprene (PI) of molecular mass between 1,000,000 and 2,000,000 daltons is dissolved in cyclohexane with stirring so as to obtain a solution containing 7 mass % of PI.

Preparation of the disperse phase (phase B);

Bardac® (dimethyldidecylammonium chloride) is dissolved with stirring in polyethylene glycol of molecular mass 400 daltons (PEG400) so as to obtain a solution containing 10% of Bardac®.

This solution is heated at 60° C. and polyethylene oxide of molecular mass of 5000 daltons (PEO 5000) is added with stirring until a clear solution containing 10% by weight of PEO 5000 is obtained.

The temperature of the mixture 60° C. corresponds to a temperature higher than the gel-liquid transition temperature (Ttrans), which is determined as the abrupt change in the viscosity of the mixture at this temperature and is, in this case, 45°–50° C.

Preparation of the gel dispersion 5.52% of phase B (consisting of a mixture of PEO 5000, PEG400 and Bardac®), on a mass basis relative to the phase A, is added at 60° C. with stirring to the phase A, that is to say to the solution of PI in cyclohexane.

At ambient temperature (20° C.) a dispersion, stable for at least 12 hours, of a virucidal gel is thus obtained, in which the particle size is on average from 3 to 5 $\mu$m.

The size of the inclusions can be adjusted by control of the stirring speed and of the rate of cooling after dispersion.

The structure of the gel dispersion is illustrated in FIG. 1.

ii) Preparation of an elastomer film

The organic solvent is evaporated at atmospheric pressure from the dispersion previously produced at 20° C.

An elastomer film is obtained enclosing gel inclusions the size of which is on average from about 3 to 5 $\mu$m.

The inclusions are dispersed uniformly in the elastomer and are in gel form at ambient temperature.

They represent approximately 40 mass % of the material and their composition is that of the phase B, defined above, namely: 10% of PEO 5000, 9% of Bardac® and 81% of PEG400.

The structure of the gel dispersion in the film is illustrated in FIG. 2.

EXAMPLE 2

An elastomer film according to the present invention, based on SEBS, containing inclusions of a reversible gel including PEO 5000 as structuring polymer c and not comprising any crosslinking agent $d_{rc}$.

The operation is carried out as in Example 1, the polyisoprene being replaced with synthesis SEBS (styrene ethylene butylene styrene) (of total molecular mass of 53,000 daltons and in which the PS weight content is 29%).

The SEBS is dissolved with stirring and at 30° C. in a predominantly naphthenic solvent, so as to obtain a solution containing 15 mass % of SEBS.

The preparation of the phase B (virucidal gel) and its dispersion in the phase A defined above are carried out according to the method described in Example 1.

EXAMPLE 3

An elastomer film according to the present invention, based on SEBS, containing inclusions of a reversible gel including PEO 5000 as structuring polymer c and not containing any crosslinking agent $d_{rc}$.

The operation is carried out as in Example 2, but with variation in the proportions of the constituent mixture of the gel (PEO 5000, PEG400 and Bardac®).

The combinations of the mixture resulting in a gel at ambient temperature are bounded by the phase diagram illustrated in FIG. 3, in which the shaded domain corresponds to the domain of existence of the gel at 20° C.

The PEG400 content is decreased from 81% to 63.6% and then to 45.5% relative to the phase B, while the PEO 5000 content is increased respectively to 27.4%, than to 45.5%, the mass content of Bardac® being kept constant at 9% (also expressed as mass content in relation to the phase B).

The combinations produce a gel which can be dispersed according to the conditions of Example 1.

Furthermore, Bardac® can be employed alone or as a mixture with other compounds which have a virucidal activity, f for example, chlorhexidine digluconate.

When the Bardac® is replaced in the above gel composition with one of the following mixtures;

90% of Bardac® 2270E containing 70% of active principle+10% of chlorhexidine digluconate, or 80% of Bardacs® 2270E containing 70% of active principle+20% of chlorhexidine digluconate, or 75% of Bardac® 2270E containing 70% of active principle+25% of chlorhexidine digluconate, a gel is obtained at ambient temperature, producing, according to the conditions of Example 1, a stable dispersion.

EXAMPLE 4

An elastomer film according to the present invention, based on SEBS, containing inclusions of a reversible gel including PEO m as structuring polymer c, m being between about 2000 and 100,000 and not containing any crosslinking agent $d_{rc}$.

The operation is carried out as in Example 2, the PEO 5000 being replaced with another PEO, of different molecular mass, that is PEO m, m denoting the total molecular mass and being between about 2000 and 100,000.

In these conditions a stable dispersion of size between about 1 and 25 $\mu$m is obtained; the film obtained after evaporation of the solvent encloses a homogeneous dispersion of gel inclusions of size between 1 and 25 $\mu$m.

EXAMPLE 5

An elastomer film according to the present invention based on polyisoprene or an SEBS, containing inclusions of a reversible gel including gelatin as structuring polymer c and not comprising any crosslinking agent $d_{rc}$.

The operation is carried out as in Example 1 or in Example 2, the PEO 5000 being replaced with gelating produced by acid treatment of collagen and with a Bloom number of 175.

Preparation of the disperse phase (phase B):

Gelatin is dissolvent with stirring at 60° C. in a mixture of Bardac® and of ethylene glycol containing 25 mass % of Bardac®.

The clear solution formed contains 14.3 mass % of gelatin.

The temperature of the mixture (60° C.) corresponds to a temperature higher than the gel-liquid transition temperature, which is determined as an abrupt change in the viscosity of the mixture at this temperature and is 30°–35° C. in the present case.

Preparation of the gel dispersion:

In the same manner as in Example 1, 5.52 mass % of phase B, relative to the phase A, is added with stirring at 60° C.

At ambient temperature, a dispersion, stable for at least 12 hours, of virucidal gel is obtained, in which the particle size is on average from 1 to 10 µm.

The elastomer film obtained by evaporation of the organic solvent at 20° C. at atmospheric pressure enclosed gel inclusions the size of which is on average from 1 to 10 µm. Their composition is that of the phase B, namely: 14.3% of gelatin, 64.3% of ethylene glycol and 21.4% of Bardacs®.

EXAMPLE 6

An elastomer film according to the present invention, based on polyisoprene or on SEBS, containing inclusions of a reversible gel including gelatin as structuring polymer c and not comprising any crosslinking agent $d_{rc}$.

The operation is carried out as in Example 5, the Bardac® being replaced with an iodine complex of polyvinylpyrrolidone (marketed by the company Aldrich under reference 86,056-5).

Preparation of the disperse phase (phase B):

Gelatin is dissolved with stirring at 60° C. in a mixture containing the iodine complex of polyvinylpyrrolidone, water and polyethylene glycol 400 in the following proportions based on mass: 14.5% of gelatin, 72.7% of water, 5.5% of iodine complex and 7.3% of polyethylene glycol 400.

The clear blood-red solution formed contains 14.5 mass % of gelatin.

The temperature of the mixture (60° C.) corresponds to a temperature higher than the gel-liquid transition temperature, which is determined as an abrupt change in the viscosity of the mixture at this temperature and is 30°–35° C. in the present case.

The combinations of the mixture resulting in a gel at ambient temperature are bounded by the phase diagram illustrated in FIG. 4 in which the shaded domains 1, 2 and 3 correspond to the claimed domains of composition: the domain 1, bounded by a solid line, corresponds to a gelatin/water mass ratio R of 1/4, the domain 2, bounded by a broken line, corresponds to a gelatin/water mass ratio R of 1/8 and the domain 3, bounded by dots, corresponds to a gelatin/water mass ratio R of 1/16.

The preparation of the gel dispersion is carried out similarly to that of Example 5, that is to say that 5.52 mass % of phase B thus formed, relative to the phase A, is dispersed; the dispersion thus produced is stable for 12 hours and the film encloses inclusions of size between 1 and 25 µ.

EXAMPLE 7

The operation is carried out as in Examples 5 and 6, the same components also being employed. However, the proportion of phase B is changed from 10% to 80% relative to the final film. In these conditions a stable dispersion is obtained in which the particle size of the disperse phase varies between 0.1 and 25 µm.

EXAMPLE 8

An elastomer film according to the present invention, based on polyisoprene or on SEBS, containing inclusions of a reversible gel including polyvinyl alcohol as structuring polymer c and comprising a crosslinking agent $d_{rc}$; borax.

In this example the structuring polymer c is polyvinyl alcohol of Mowiol® 28-99 type, characterized by a molecular mass of 88,000 daltons and a percentage of hydrolysis of 99%. Its viscosity in a 4% solution in water is 28 mpas.

The preparation of the phase A is similar to that of Example 1 or of Example 2.

Preparation of the disperse phase (phase B):

Mowiol® is dissolved with stirring at 80° C. in water (solvent $d_s$) to obtain a solution containing 2.5% of Mowiol®.

Triton X100® (active chemical substance x) is added to this solution with stirring until a clear solution is obtained containing 10% of Tritons (expressed in relation to the Mowiol® solution).

Preparation of the gel dispersion:

In a manner similar to Example 1 or Example 2, 5.52 mass % of phase B relative to the phase A is added with stirring and at 30° C. Finally, the gel is produced by adding borax, in a mass content of 5% (expressed in relation to the Mowiol® solution).

At ambient temperature, a dispersion of virucidal gel is obtained which is stable for at least 12 hours and in which the particle size is on average from 1 to 5 µm.

The elastomer film obtained by evaporation of the organic solvent at 20° C. at atmospheric pressure encloses gel inclusions the size of which is on average from 1 to 5 µm.

EXAMPLE 9

An elastomer film according to the present invention, based on polyisoprene or on SEBS, containing inclusions of an irreversible gel including polyvinyl alcohol as structuring polymer c and comprising a crosslinking agent $d_{ic}$: glutaraldehyde.

The operation is carried out as in Example 8, the same components being also employed in the same proportions.

However, the type of crosslinking agent is changed, borax being replaced with glutaraldehyde (irreversible crosslinking agent).

Preparation of the disperse phase (phase B):

Mowiol® is dissolved with stirring and at 80° C. in water to obtain a solution containing 2.5% of Mowiol®.

Triton X100® is added to this solution with stirring until a clear solution is obtained containing 10% of Triton® (expressed in relation to the Mowiol® solution).

Preparation of the gel dispersion:

In a way similar to that in Example 1, 5.52 mass % of phase B, relative to the phase A, is added with stirring and at 50° C.

The gel is next produced by crosslinking the polyvinyl alcohol in acidic medium by adding, with stirring, 0.475% (mass content expressed in relation to the Mowiol® solution) of a solution containing 0.005% of glutaraldehyde (based on mass) in a water: hydrochloric acid mixture containing 9 parts of water per part of molar acid.

At ambient temperature a dispersion, stable for at least 12 hours, of virucidal gel is obtained, in which the particle size is on average 1 to 5 µm.

The elastomer film obtained by evaporation of the organic solvent at 20° C. at atmospheric pressure encloses gel inclusions the size of which is on average from 1 to 5 µm.

EXAMPLE 10

Preparation of gloves, fingerstalls or sheaths or diaphragms coated with an elastomer film in accordance with the present invention.

An elastomer film in accordance with the invention is added, as coating of elastomer material, onto a layer of elastomer material previously fashioned in the desired form by the usual manufacturing techniques, as follows:

At least the layer of elastomer according to the invention is deposited, for example on a former made of ceramic, glass or similar material defining the glove, the fingerstall or the sheath or diaphragm to be manufactured; the procedure is especially as described in European Patent 0 306 389.

Having described the present invention, it will be apparent to the artisan that many changes and modifications may be made to the above-described embodiments without departing from the spirit or scope of the present invention.

What is claimed as new and is desired to be secured by Letters Patent of the United States is:

1. A protective elastomer film, comprising at least one active chemical substance in the form of a phase which is uniformly dispersed in said elastomer, wherein:
    (i) the dispersed phase of the film is in the form of a gel, reversible as a function of temperature, said reversible gel consisting essentially of:
        i) a structuring polymer (c),
        ii) a solvent ($d_s$) for the structuring polymer (c),
        iii) at least one active chemical substance (x),
        iv) a reversible crosslinking agent ($d_{rc}$),
        said reversible gel being in the form of inclusions within said elastomer film; and
    (ii) said elastomer is selected from the group consisting of polybutadiene, polyisoprene, SBR (styrene butadiene rubber), NBR (nitrile butadiene rubber), SBS (styrene butadiene styrene), SIS (styrene isoprene styrene) SEBS (styrene ethylene butylene styrene) copolymers, and mixtures thereof.

2. The elastomer film of claim 1, wherein said reversible gel has a gel-liquid transition temperature (Ttrans) of between 0° C. and 120° C.

3. The elastomer film of claim 1, wherein the gel comprises:
    a) between about 25 and 97% by weight of solvent ($d_s$), relative to the gel,
    b) between about 1 and 74% by weight of the structuring polymer (c), relative to the gel,
    c) between about 1 and 74% by weight of the active chemical substance (x), relative to the gel, and
    d) crosslinker ($d_{rc}$) is present and in an amount of up to 1% by weight of crosslinker/total constituents.

4. The elastomer film of claim 1, wherein the structuring polymer (c) is hydrophilic and miscible with the elastomer phase.

5. The elastomer film of claim 1, wherein the structuring polymer (c) is selected from the group consisting of crystallizable polymers, partially crystallizable polymers, and polymers which were not organized in the solid state.

6. The elastomer film of claim 5, wherein said structuring polymer (c) is selected from the group consisting of polyethers, gelatin, gums, pectins, alginates, methyl cellulose, hydroxyethyl cellulose, hydroxypropyl cellulose, carboxymethyl cellulose, polyethyleneimine, polyacrylic acid, polyacrylates, polymethacrylates and poly (vinyl methyl ether).

7. The elastomer film of claim 1, wherein the solvent ($d_s$) is selected from the group consisting of polyols and polyethylene glycols which are liquid at ambient temperature and having a molecular weight of between 62 and 750 daltons, and water, employed alone or as a mixture.

8. The elastomer film of claim 7, wherein said polyols are selected from the group consisting of ethylene glycol and glycerine.

9. The elastomer film of claim 1, wherein the crosslinker ($d_{rc}$) is selected from the group consisting of boric acid, borax, aluminum hydrate, aluminum hydroxides, and divalent metals.

10. The elastomer film of claim 1, which comprises polyvinyl alcohol as the structuring polymer (c), water as solvent ($d_s$) and borax as reversible crosslinking agent ($d_{rc}$).

11. A process for the preparation of the elastomer film of claim 1, which comprises:
    1) preparing a dispersion of a gel, which comprises:
        a) preparing a phase A by dissolving the elastomer in an organic solvent (a);
        b) preparing a phase B (gel) and dispersing said phase B in the phase A, said phase B being prepared by mixing at least one active chemical substance (x) in a solvent ($d_s$), followed by mixing of the solution obtained with a structuring polymer (c), then by dispersing this phase B and the phase A before addition of the crosslinker ($d_{rc}$); and
    2) evaporating the organic solvent (a), to obtain an elastomer film containing gel inclusions in a stable dispersion form.

12. The process of claim 11, wherein the evaporation of the solvent is performed at a temperature lower than Ttrans.

13. The process of claim 11, wherein the organic solvent (a) is selected from the group consisting of aromatic, aliphatic and alicyclic hydrocarbons.

14. The process of claim 13, wherein the organic solvent (a) is selected from the group consisting of paraffinic hydrocarbons, cyclohexane, benzene, toluene, xylene, tetralin, decalin, petroleum cuts and a mixture thereof.

15. A dispersion for the preparation of the elastomer film of claim 1, which comprises:
    i) a phase A comprising an elastomer dissolved in an organic solvent (a) which is defined in claim 13,
    wherein in which is dispersed, in the form of a reversible gel, a phase B comprising an active chemical substance (x) included in a structuring polymer (c), a solvent ($d_s$), and a reversible crosslinking agent ($d_{rc}$).

16. A process for preparing the dispersion of claim 15, which comprises:
    1) preparing a phase A by dissolving the elastomer in an organic solvent (a); and
    2) preparing a phase B (gel) by mixing at least one active chemical substance (x) in a solvent ($d_s$), followed by mixing of the solution obtained with a structuring polymer (c), then dispersing said phase B and phase A before addition of the crosslinking agent ($d_{rc}$).

* * * * *

UNITED STATES PATENT AND TRADEMARK OFFICE
CERTIFICATE OF CORRECTION

PATENT NO. : 5,883,155

DATED : March 16, 1999

INVENTOR(S): Pierre HOERNER et al

It is certified that an error appears in the above-identified patent and that said Letters Patent is hereby corrected as shown below:

In the drawings:

Figure 1 should read " Phase A: Elastomer + Solvent "

$$(X) \quad\quad \text{Phase B}$$
$$(C)$$
$$--(d_s)--$$

FIG. 1

Figure 2 should read "Phase A: Elastomer "

$$(X) \quad\quad \text{Phase B}$$
$$(C)$$
$$--(d_s)--$$

FIG. 2

Signed and Sealed this

Fourth Day of July, 2000

Attest:

Q. TODD DICKINSON

*Attesting Officer*     *Director of Patents and Trademarks*